(12) United States Patent
Stamatoyannopoulos et al.

(10) Patent No.: US 6,184,343 B1
(45) Date of Patent: Feb. 6, 2001

(54) FETAL GLOBIN INDUCING FACTOR

(76) Inventors: George Stamatoyannopoulos; Thalia Papayannopoulou, both of 702 35th Ave., Seattle, WA (US) 98122

( * ) Notice: Under 35 U.S.C. 154(b), the term of this patent shall be extended for 0 days.

(21) Appl. No.: 08/986,304

(22) Filed: Dec. 5, 1997

Related U.S. Application Data (60) Provisional application No. 60/033,247, filed on Dec. 6, 1996.

(51) Int. Cl.[7] .................................................. C07K 14/47
(52) U.S. Cl. ........................ 530/300; 530/324; 530/350
(58) Field of Search .................................. 530/300, 350, 530/324, 325, 326, 327, 328, 329, 330; 514/12

(56) References Cited

PUBLICATIONS

Berendsen, Science, vol. 282, pp. 642–643, Oct. 1998.*
Caldwell, Yakubutsu Dotai (Xenobiotic Matabolism and Disposition), vol. 11(1), pp. 119–125, 1996.*

\* cited by examiner

*Primary Examiner*—Terry McKelvey
(74) *Attorney, Agent, or Firm*—Baker Botts, L.L.P.

(57) ABSTRACT

The invention is directed to fetal globin inducing factor (FGIF), and to nucleic acids encoding FGIF. FGIF controls the expression of fetal globin gene products. An FGIF polypeptide is shown in FIG. 3 and nucleotide sequences that encode FGIF polypeptides are shown in FIGS. 1 and 2. The invention is also directed to therapeutic methods employing FGIF polypeptides, encoding nucleic acids and functional fragments thereof for the treatment of globin disorders and to methods for screening compounds that modulate fetal globin gene expression as well as compounds identified by these methods.

4 Claims, 6 Drawing Sheets

FIG. 1

```
   1 gaacccggaa gtgagatgca aggcggcgat tttcccttct gtcagatctt
  51 gatgaacaaa gcagtcataa ttcatctcta gaaagattta tatcctggca
 101 tttgaaatgc tttttattta gaatagtagt aaaaAATGga aaaagaaaaa
 151 ggaaatgatg atggaatacc agaccaagag aattccttGg attttctga
 201 acactttagc caacttgaat tgttggaaac acatggacac cttattccta
 251 ctggtactca aagtctttgg gtaggcaatt ctgatgaaga tgaggagcaa
 301 gatgacaaaa atgaagagtg gtatcgattg caagaaaaaa aAAtggAaaa
 351 agacccaagc agattgcttc TTTgggcTgc tgaaAAAAAT CGgCTTACCA
 401 CAGTGCGGAG ACTCCTTTCT GAAAAGGCCa CTCACGTGAA CACTAGGGAT
 451 GAAGATGaGT ATACCCCTCT TCATCGAGCA GCCTACAGTG GACACTTAGA
 501 TATTGTTCag gagctcattg cacaggggc cgatgttcat gcagtgactg
 551 tggatggctg gacgcccctg cacagtgctt gtaagtggaa taataccaga
 601 gtggcttctt tcttactgca gcatgatgca gatatcaatg cccaaacaaa
 651 aggcctcttg accccttGc atcttgctgc tgggaacaga gacagcaagg
 701 atacctaga actcctcctg atgaaccgtt acGtcaaacc agggctgaaa
 751 aacaacttgg aagaaactgc atttgatatt gccaggagga caagtatcta
 801 tcactacctc tttgaaattg tggaaggctg tacaaattct tcacctcagt
 851 cttaacaatt ctagtaattt tcctaagttt ctaaatacca gtgcctcctg
 901 tgtgtgagat gtattcccat aatcaaagtt gacgtcaaac atcttactac
 951 aaaaattcag tgacatttat tataacattc ttccaagtga attgcctgac
1001 tttgatgtca aatgtatttg aaagtaattt gcatatatct ttaattattt
1051 ctgtggagtt tgtgattttt ttatcagaaa taatttaat gtgtgtatac
1101 ttaaaaactt gacacgggtt gtacagaaac tggtattttt ggtGctgata
1151 caagagaaat gtatttaa atatcccaca tcctggatct ttGttgggta
1201 tttagtatat tgacatatat ttttataagg tGaggtaact cagaacttaa
1251 tttaaAAGtc ttaaatattc tgatacaatt caGctgtctT ctctAccttA
1301 ccatagccat gtctctGc (SEQ ID NO.1)
```

FIG. 2a

```
              10         20         30         40         50
falf.t  GAACCCGGAAGTGAGATGCAAGGCGGCGATTTTCCCTTCTGTCAGATCTT-GA------T
        |||||||||| || | |   |:| || :||| | ||||| | |  || ||
abahyb  AACCCGGAAAGGAAGTTC---TCNGTGAGNTTCTC-TCTGTGAAAGGTTAGAAAGAATC
              10         20         30        40         50

60         70         80         90        100        110
falf.t  GAACAAAGCAGTCATAATTCATCTCTAGAAAGATTTATATCCTGGCATTTGAAATGCTTT
        ||||| :||| |||||||||||||  |||||| ||   ||| | | ||||||||||||||
abahyb  AAACAATNCAGACATAATTCATCTCCTTAAAGA-TTGCGCCCTAGTACTTGAAATGCTTT
              60         70         80         90        100        110

120        130        140        150        160        170
falf.t  TTATTTAGAATAGTAGTAAAAAATGGAAAAAGAAAAAGGAAATGATGATGGAATACCAGA
        ||||||| || |||||| |||||||||||||||||||||   ||| |||||| || ||||||
abahyb  TTATTTAAAAGAGTAGT-AAAAATGGAAAAAGAAAA---AAAGGATGATGAAAAACCAGA
             120        130        140        150        160        170

180        190        200        210        220        230
falf.t  CCAAGAGAATTCCTTGGATTTTTCTGAACACTTTAGCCAACTTGAATTGTTGGAAACACA
        ||| || |: || |||||||||||||||| |||| ||| |||||||||||||| |||| ||
abahyb  CCAGGAAANCTCTGTGGACTTTTCTGAACAGTTTAACCAGCTTGAATTGTTGAAAACTCA
             180        190        200        210        220        230

240        250        260        270        280        290
falf.t  TGGACACCTTATTCCTACTGGTACTCAAAGTCTTTGGGTAGGCAATTCTGATGAAGATGA
        |||||||||  |||||  |||||||||||| |||||  ||||||||||||||||||||||||
abahyb  TGGACACCTGATTCCCACTGGTACTCAGAGTCTCTGGGTAGGCAATTCTGATGAAGATGA
             240        250        260        270        280        290

300        310        320        330        340        350
falf.t  GGAGCAAGATGACAAAAATGAAGAGTGGTATCGATTGCAAGAAAAAAAATGGAAAAAGA
        |||:|||| || ||||| ||||||||||| | |||||||||||||||||| ||||||||||
abahyb  AGAGNAAGAGGAAAAAAACGAAGAGTGGTACCAATTGCAAGAAAAAAAGATGGAAAAAGA
             300        310        320        330        340        350

360        370        380        390        400        410
falf.t  CCCAAGCAGATTGCTTCTTTGGGCTGCTGAAAAAAATCGGCTTACCACAGTGCGGAGACT
        |||||||  |||||||||||||||||||||||||||||||| | |||||| |||||||||
abahyb  TCCAAGCAAATTGCTTCTTTGGGCTGCTGAAAAAAATCGGCTTGCTACAGTGCAGAGACT
             360        370        380        390        400        410

420        430        440        450        460        470
falf.t  CCTTTCTGAAAAGGCCACTCACGTGAACACTAGGGATGAAGATGAGTATACCCCTCTTCA
        || |||| ||||||| || | | |||||||||||||||||||||||||||||||||||||
abahyb  ACTCTCTGAGAAGGCCGCTGAAGTGAACACTAGGGATGAAGATGAGTATACCCCTCTTCA
             420        430        440        450        460        470

480        490        500        510        520        530
falf.t  TCGAGCAGCCTACAGTGGACACTTAGATATTGTTCAGGAGCTCATTGCACAGGGGGCCGA
        |||||||||||||||||| || ||||| |||||| |||||  | || ||||||| ||
abahyb  CCGAGCAGCCTACAGTGGGCATATAGATGTTGTTCGTGAGCTGGTGGCTAAGGGGGCAGA
             480        490        500        510        520        530

540        550        560        570        580        590
falf.t  TGTTCATGCAGTGACTGTGGATGGCTGGACGCCCCTGCACAGTGCTTGTAAGTGGAATAA
        |||||||||||||||||||||||||||||| ||||| |||||||||||||||||||||||
```

FIG. 2b

```
abahyb TGTTCATGCAGTGACTGTGGATGGCTGGACACCACTGCATAGTGCTTGTAAGTGGAATAA
              540       550       560       570       580       590
              600       610       620       630       640       650
falf.t TACCAGAGTGGCTTCTTTCTTACTGCAGCATGATGCAGATATCAATGCCCAAACAAAAGG
       ||||| ||||| |||||||||||| |||||||||||||| ||||| |||||||||| |||||
abahyb TACCAAGGTGGCCTCTTTCTTACTTCAGCATGATGCAGACATCAACGCCCAAACGAAAGG
              600       610       620       630       640       650

660       670       680       690       700       710
falf.t CCTCTTGACCCCCTTGCATCTTGCTGCTGGGAACAGAGACAGCAAGGATACCCTAGAACT
       ||| ||||||||| ||||| |||||||||||||||||||||||||| || || || |||||
abahyb CCTTTTGACCCCCTTTGCACCTTGCTGCTGGGAACAGAGACAGCAGAGACACTCTGGAACT
              660       670       680       690       700       710

720       730       740       750       760       770
falf.t CCTCCTGATGAACCGTTACGTCAAACCAGGGCTGAAAAACAACTTGGAAGAAACTGCATT
       |||||||||||| |||||| |||||||||| |||||| ||||||| |||||||||||| |
abahyb CCTCCTGATGAATCGTTACATCAAACCAGAGCTGAAGAACAACTCACAAGAAACTGCTTC
              720       730       740       750       760       770

780       790       800       810       820       830
falf.t TGATATTGCCAGGAGGACAAGTATCTATCACTACCTCTTTGAAATTGTGGAAGGCTGTAC
       |||||| ||||||||||||||| ||||||||||||||||||||||| ||||||||| |||
abahyb TGATATCGCCAGGAGGACAAGCATCTATCACTACCTCTTTGAAATTGCGGAAGGCTCTAC
              780       790       800       810       820       830

840       850       860       870       880       890
falf.t AAAATTCTTCACCTCAGTCTTAACAATTCTAGTAATTTTCCTAAGTTTCTAAATACCAGTG
       ||| ||||||||||| |||||||| | ||||||||| ||||||||| || ||||||||
abahyb AAACTCTTCACCTCCGTCTTAATGACTCTAGTAATTT---TAAGTTTCAAAGTACCAGTG
              840       850       860       870       880

900       910       920       930       940       950
falf.t CCTCCTGTGTGTGAGATGTATTCCCATAAT-CAAAGTTGACGTCAAACA--TCTTACTAC
       ||||| ||||| ||||||||     |||  | || ||  |  ||| |  |||  |||||
abahyb CCTCCCATGTGTGAGATGTA---AAATATTCCCATGTACAGAGAAAAGATGTCTCACTAC
              890       900       910       920       930       940

960       970       980       990      1000      1010
falf.t AAAAATTCAGTGACATTCATTATAACATTCTTCCAAGTGAATTGCCTGACTTTGATGTCA
       ||| ||| ||     :: ||  |  |||||||||||| |||| ||| ||||||||||||
abahyb AGAAGTTCTGTTGTGNGNATCACAGCTTTCTTCCAAGTAAGCTGCCCGACCTTGATGTCA
              950       960       970       980       990      1000

1020      1030      1040      1050      1060      1070
falf.t AATGTATTTGAAAGTAATTTGCATATATCTTTAATTATTTCTGTGGAGTTTGTGATTTTT
       |||||||||| || ||||| || |||| |  ||||| || ||| |||| |||   |||
abahyb CATGTATTTGAGAGGTATTTGGGTACATCTGTGGAGATTTC--TGCAGTGTGTG--GTTT
             1010      1020      1030      1040      1050      1060

1080      1090      1100      1110      1120      1130
falf.t TTATCAGAAATAATTTTAATGTGTGTATACTTAAAAACTTGACACGGGTTGTACAGAAAC          (SEQ ID NO.2)
       ||||||||||||||||||||
abahyb TTATCAGAAATAATTTTGCAGGACACAGGTAATACAGAAACTAAGGATATTTTTTGGTGC        (SEQ ID NO.3)
             1070      1080      1090      1100      1110      1120
```

FIG. 3

```
  1 MEKEKGNDDG IPDQENSLDF SEHFSQLELL ETHGHLIPTG TQSLWVGNSD
 51 EDEEQDDKNE EWYRLQEKKM EKDFSRLLLW AAEKNRLTTV RRLLSEKATH
101 VNTRDEDEYT PLHRAAYSGH LDIVQELIAQ GADVHAVTVD GWTPLHSACK
151 WNNTRVASFL LQHDADINAQ TKGLLTPLHL AAGNRDSKDT LELLLMNRYI
201 KPGLKNNLEE TAFDIARRTS IYNYLFEIVE GCTNSSPQS* (SEQ ID NO.4)
```

FETAL GLOBIN INDUCING FACTOR

CROSS-REFERENCE TO RELATED APPLICATIONS

This application claims the benefit of U.S. Provisional Patent Application Ser. No. 60/033,247, filed Dec. 6, 1996.

FIELD OF THE INVENTION

This invention relates to nucleic acids that encode fetal globin inducing factor and to fetal globin inducing factor. The invention also relates to methods for altering globin expression by the regulation of globin transcription.

BACKGROUND OF THE INVENTION

Oxygen is transported throughout multicellular animals through the function of hemoglobin. The most primitive of these oxygen-carrying molecules, or globins, is a single polypeptide of about 150 amino acid residues and is utilized in worms, insects, and primitive fish. In higher adult vertebrates two types of globin chains exist. These chains are referred to as the $\alpha$ and $\beta$ globins and make up a tetrameric hemoglobin molecule composed of two $\alpha$ and two $\beta$ chains, or $\alpha_2\beta_2$. Through a series of gene duplications during evolution, other globin chains also exist and exhibit developmental and stage specific expression. These other globins include $\gamma$ globin which is specifically expressed in the fetus to produce an $\alpha_2\gamma_2$ hemoglobin. This fetal hemoglobin exhibits higher affinity for oxygen than adult $\alpha_2\beta_2$ hemoglobin. Another globin chain arising during evolution is the $\delta$ globin which gives rise to the minor hemoglobin $\alpha_2\delta_2$ found in adult primates. Finally, an $\epsilon$ globin also exists which results in another embryonic form of hemoglobin having the composition $\alpha_2\epsilon_2$.

Abnormalities in the structure or in the rate of synthesis of the various globin chains result in a variety of different pathological conditions which can be classified into two distinct groups (Stamatoyannopoulos and Nienhuis, *Molecular Basis of Blood Diseases*, Stamatoyannopoulos et al. (eds.), Philadelphia pp. 108–136, 1994; D. J. Weatherall, *Molecular Basis of blood Diseases*, Stamatoyannopoulos et al. (eds.), Philadelphia pp. 161–195, 1994; and Bunn, H. F., *Molecular Basis of Blood Diseases*, Stamatoyannopoulos et al. (eds.), Philadelphia pp. 208–244, 1994).

The first classification is where structural abnormalities of $\alpha$ or $\beta$ globin genes exist. These abnormalities are called hemoglobinopathies. There are over 500 different mutations of $\alpha$ or $\beta$ globin genes producing abnormal hemoglobins. The most common hemoglobinopathy is the sickle hemoglobin or hemoglobin S (Hb S) which represents the substitution of valine for glutamic acid in position six of the $\beta$ globin subunit. The sickle cell gene is frequent among Black people; about eight to ten percent of African-Americans carry the Hb S gene while in certain populations of Africa, like in Nigeria, twenty-five percent of the population carries sickle cell trait. There are about 120,000 new cases of sickle cell disease born each year. It is estimated that the prevalence of homozygous Hb S patients in the United States is between 60,000 and 80,000. Sickle cell disease is a severe disease characterized by frequent painful crises, hemolytic anemia and severe organ damage due to intravascular sickling. The life span of these patients is significantly decreased.

Evidence now indicates that elevated levels of fetal hemoglobins (Hb F) attenuate the severity of sickle cell disease. As is well known, Hb S molecules tend to form long, intracellular polymers upon deoxygenation. Physiological effects of sickle cell mutations are due, in large part, to abnormalities in the rheological properties of blood. The rate of sickle cell hemoglobin polymerization is largely dependent on the concentration of Hb S in the red cell. The presence of fetal hemoglobin in sickle red cells affects Hb S polymerization by decreasing the concentration of the abnormal molecule and, most importantly, by failing to participate in polymer formation. In addition to this biochemical evidence, genetic evidence similarly indicates that high levels of Hb F have therapeutic effects in sickle cell disease. For example, compound heterozygotes inheriting a sickle cell gene and a gene for hereditary persistence of fetal hemoglobin have no clinical manifestations when Hb F exceeds twenty-five percent of total hemoglobin content (75% of hemoglobin in these patients is Hb S). Similar observations exist for persons who carry the combination of the sickle cell gene and a condition called $\delta\beta$ thalassemia which is associated with high levels of Hb F.

The levels of Hb F required for therapeutic benefit in sickle cell disease have been investigated in several studies. In a prospective study, Hb F levels in excess of ten percent were associated with fewer episodes of aseptic necrosis, while levels greater than twenty percent were associated with fewer painful crises and pulmonary complications. In a large prospective study of the natural history of sickle cell disease, the frequency of painful crises was found to be inversely proportional to the square of the Hb F level. These results indicate that even modest elevations in Hb F can yield therapeutic benefits. It is generally accepted that production of over twenty-five percent fetal hemoglobin in the red cell can cure sickle cell disease.

The second classification is where abnormalities in globin chain synthesis exist. These abnormalities are called $\alpha$, $\beta$, or $\delta\beta$ thalassemia syndromes. An example of these abnormalities is the $\beta$ thalassemia syndromes. Beta ($\beta$) thalassemia genes are common among people of Mediterranean and Asian descent. About 100,000 patients with homozygous thalassemia, or combinations of $\beta$ thalassemia with abnormal hemoglobins, are born each year in this area of the world. In $\beta$ thalassemia there is either a total absence or a severe deficiency of $\beta$ globin gene. However, $\alpha$ chain production continues at normal levels. These excess $\alpha$ globin chains accumulate and precipitate within erythroblasts resulting in ineffective erythropoiesis and cell death, both of which are characteristic of the thalassemia syndromes.

Precipitation of $\alpha$ chains in circulating erythrocytes and consequential membrane damage is responsible for the hemolytic syndrome. Patients with homozygous $\beta$ thalassemia survive beyond the period of the switch from fetal to adult globin formation because some level of Hb F production continues in the adult stage of development. Sufficient $\gamma$ gene expression occurs in only a small proportion of erythroblasts. Cells which contain adequate levels of Hb F survive and thereby provide red cells which are released in the periphery. The efficiency of $\gamma$ globin production in erythroblasts of patients with $\beta$ thalassemia clearly determines the severity of their clinical course. It is accepted that any increase of fetal hemoglobin will have therapeutic effects in $\beta$ thalassemia syndromes. Production of over twenty-five percent of fetal hemoglobin per cell can cure the disease of patients with homozygous $\beta$ thalassemia.

Attempts have been made to augment the expression of fetal hemoglobin for the therapeutic treatment of sickle cell disease or homozygous $\beta$ thalassemia (Blau and Stamatoyannopoulos, *Hematology Trends* '93, Lechner et al.

(eds.), Stuttgart-New York, pp 144–158, 1993). For example, 5-azacytidine induces fetal hemoglobin in animals and patients with thalassemia or sickle cell disease. However, its use was discontinued because it has been shown that this drug is carcinogenic. Hydroxyurea, a cytotoxic drug used in cancer chemotherapy, has also been shown to induce fetal hemoglobin in experimental animals. This compound kills mature erythroid cells and induces a fast downstream differentiation of immature cells. Treatment of sickle cell patients with hydroxyurea results in induction of fetal hemoglobin which reaches therapeutic levels in a small proportion of patients. However, induction of fetal hemoglobin occurs only when blood cytotoxicity appears as measured by decreased white blood cell counts. Furthermore, issues related to the wisdom of life long treatment with a cytotoxic drug which may also be carcinogenic remain especially for the treatment of children. Further, a large portion of patients respond to the hydroxyurea treatment with only small or moderate elevations of fetal hemoglobin. Hydroxyurea does not induce fetal hemoglobin in patients with homozygous β thalassemia.

Another form of treatment involves intravenous administration of arginine butyrate. This compound induces fetal hemoglobin synthesis in primates and has been reported to induce fetal hemoglobin in patients with homozygous β thalassemia receiving continuous IV infusion of butyrate for two to three weeks. However, a second study in which patients with homozygous β thalassemia or Hb S disease were treated with continuous intravenous (IV) infusion of butyrate for up to two or three months did not reproduce these results. Most recently intermittent IV treatment with butyrate (two days every 15 days) has been shown to increase fetal hemoglobin in a few patients. It is still unclear whether this treatment can increase fetal hemoglobin to the levels required for a cure or a significant clinical improvement. Also, the side effects of treating children with IV administration of butyrate have not been determined.

Although it is generally accepted that induction of fetal hemoglobin can cure patients with Hb S disease or β thalassemia, there is a need for better compositions and methods which augment the regulation of globin gene expression.

SUMMARY OF THE INVENTION

The present invention overcomes the problems and disadvantages associated with current strategies and designs and provides new compositions and methods for the regulation of globin gene expression.

One embodiment of the invention is directed to proteins and peptides that encode fetal globin inducing factor (FGIF). This factor, and active portions thereof, can function to regulate the expression of globin genes such as fetal globin. FGIF, either purified recombinantly produced, can be used in the treatment of globin and associated disorders.

Another embodiment of the invention is directed to nucleic acids encoding FGIF and active portions thereof. FGIF proteins and polypeptides are encoded in the nucleotide sequences of FIGS. 1 and 2. These nucleic acids can be used to produce large quantities of FGIF protein, peptides, fragments or active portions thereof. The invention further comprises nucleic acid vectors containing FGIF sequences and cells, which may be eukaryotic or prokaryotic, transformed with FGIF sequences.

Another embodiment of the invention is directed to methods for regulating globin transcription. Regulation can be effected by administration of FGIF, nucleic acids that express FGIF or agents that alter FGIF expression or activity. Regulation of globin transcription can ameliorate disorders such as hemoglobinopathies and associated globin disorders. Preferably, regulation involves increasing fetal hemoglobin expression.

Another embodiment of the invention is directed to methods for screening compounds that regulate globin gene expression. Compounds identified can be used in vitro and in vivo in the treatment of globin disorders.

Other embodiments and advantages of the invention are set forth, in part, in the description which follows and, in part, will be obvious from this description or may be learned from the practice of the invention.

DESCRIPTION OF THE DRAWINGS

FIG. 1 Nucleotide sequence of the human FGIF cDNA (SEQ ID NO: 1).

FIG. 2 Comparison of the human (top) and murine (bottom) FGIF nucleotide sequence (SEQ ID NO: 2).

DESCRIPTION OF THE INVENTION

As embodied and broadly described herein, the present invention is directed to amino acid and nucleic acid sequences that encode proteins and peptides of fetal globin inducing factor and active portions thereof, and to compositions and methods for modifying the expression of globin genes.

Many attempts have been made to augment the expression of hemoglobin in humans and, in particular, fetal hemoglobin, for the therapeutic treatment of sickle cell disease, thalassemia and related disorders. Increases in Hb F levels in, for example, sickle cell patients produced fewer episodes of aseptic necrosis. Increases of greater than twenty percent were associated with fewer painful crises and pulmonary complications. In fact, the frequency of crises was found to be inversely proportional to the square of Hb F level indicating that even modest elevations in Hb F can yield therapeutic benefits.

Conventional efforts have been focused on identifying agents that simply increase Hb F levels in patients. However, the steps by which such increases can occur have largely been ignored. In efforts to analyze these steps, a factor was discovered that regulates transcription of fetal hemoglobin. That factor is referred to herein as fetal hemoglobin inducing factor (FGIF) which, as used herein, includes full length FGIF protein as well as active and functional peptides and fragments thereof.

FGIF was discovered during a systematic search for mRNAs encoding factors that induce human fetal hemoglobin genes. For this search, somatic cell hybrids were formed by fusing human fetal erythroid cells with mouse erythroleukemia cells. Initially, hybrids produce human fetal hemoglobin. After several months in culture, these hybrids switched from production of fetal hemoglobin to production of human adult hemoglobin (Papayannopoulou et al., Cell 46:469–476, 1986). Transcriptional inducers of fetal hemoglobin were sought among mRNA species that were present in both the human fetal erythroid cells and the fetal globin expressing hybrids, but absent in both the adult erythroid cells and the adult globin expressing hybrids. One such mRNA species discovered encoded FGIF.

One embodiment of the invention is directed to FGIF proteins, peptides and fragments, and active or functional portions thereof. These proteins, peptides and fragments are collectively referred to herein as FGIF. FGIF further includes amino acid sequences considered by those of ordinary skill in the art as functionally or structurally equivalent to an FGIF sequence. Methods for assessing functional and structural equivalency are well known and routine within the art. A human FGIF polypeptide comprising 239 amino acids is shown in FIG. 3.

Functionally equivalent FGIF amino acid sequences include, for example, sequences that are related in that at least one functional activity of FGIF is present. Such related, but different polypeptides include, for example, substitutions of conserved and non-essential amino acids. Functionally equivalent FGIF includes modifications of FGIF which may be made without destroying the biological function of the FGIF polypeptide. For example, only a portion of the entire primary structure may be required for effective activity. Modifications of the FGIF amino acid sequence which does not destroy its activity also fall within the definition of FGIF. Structurally equivalent FGIF sequences include genetically engineered fragments of FGIF, either individually, modified or fused to heterologous proteins such as fusion proteins that retain measurable biological activity; these also fall within the definition of the FGIF polypeptides.

Figure 3:
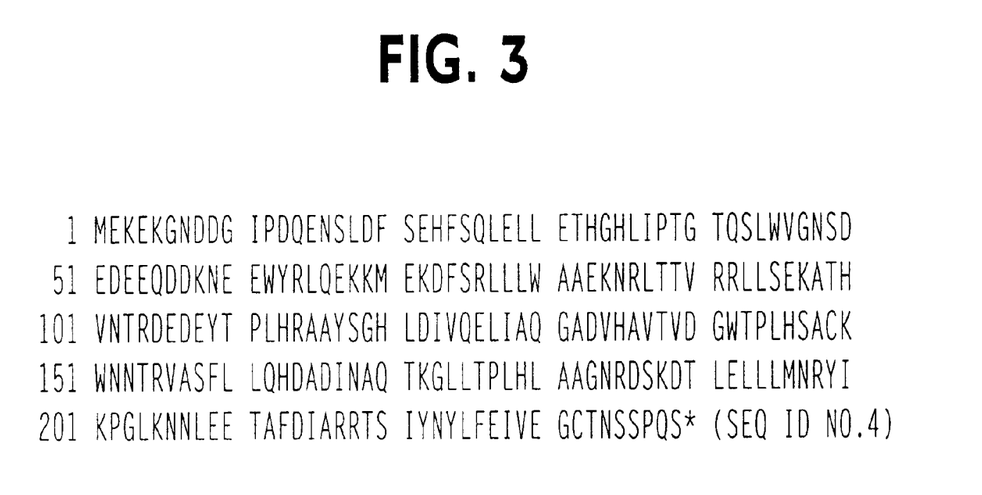
FIG. 3 Amino acid sequence of mature human FGIF comprising 239 amino acid residues that contain three ankyrin sequence motifs (SEQ ID NO: 3).

Structural and functional modification of FGIF may comprise modifications of the primary amino acid sequence of FGIF wherein the resulting polypeptides have substantially equivalent or enhanced function as compared to the sequence set forth in FIG. 3. These modifications may be deliberate, for example, through site-directed mutagenesis, or may be accidental such as through mutation in hosts which are FGIF producers. All of these modifications are included as long as FGIF biological function is retained.

Further, modified FGIF protein may comprise modification of one or more amino acids within the FGIF amino acid sequence. For example, the FGIF amino acid sequence may be altered by substituting other natural or non-natural amino acids for those present in the wild-type sequence. Natural amino acids are those commonly found in proteins from eukaryotic sources. Non-natural amino acids include chemically or biologically altered forms of natural amino acids or amino acids that are chemically synthesized. Non-natural amino acids also include unusual and modified amino acids such as, for example, aminoadipic acid, aminobutyric acid, desmosine, hydroxyproline, allo-isoleucine and many others which are well-known in the art. Modified FGIF proteins also include fusion proteins containing FGIF sequences. For example, various molecules can be attached to FGIF such as other proteins, carbohydrates, lipids, or chemical moieties. Such modifications are included within the definition of FGIF proteins and peptides.

FGIF has been purified and isolated from both human and murine sources and is present in all mammalian cells including other primate cells. Cell types that express FGIF include circulating cells, cells of the bone marrow, cells of the myeloid system. Specific cells include, for example, platelets, white blood cells, erythroid cells and their precursors such as stem cells, myeloid stem cells, erythrocyte-colony forming unit cells (E-CFU), erythrocyte-burst forming unit cells (E-BFU), and pro-erythrocytes.

FGIF can be prepared as a composition for administration in vivo or in vitro. FGIF compositions can be prepared in solution as a dispersion, mixture, liquid, spray, capsule or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil or a relatively inert solid or liquid. Liquids administered orally may include flavoring agents such as mint, cherry, guava, citrus, cinnamon, orange, mango, or mixed fruit flavors to increase palatability. Pills, capsules or tablets administered orally may also include flavoring agents. Additionally, all compositions may further comprise agents to increase shelf-life, such as preservatives, anti-oxidants and other components necessary and suitable for manufacture and distribution of the composition. Compositions further comprise a pharmaceutically acceptable carrier. Carriers are chemical or multi-chemical compounds that do not significantly alter or effect the active ingredients of the compositions. Examples include water, alcohols such as glycerol and polyethylene glycol, glycerin, oils, salts such as sodium, potassium, magnesium and ammonium, fatty acids, saccharides or polysacchaides. Carriers may be single substances or chemical or physical combinations of these substances.

As FGIF can be easily produced through recombinant technology or purification from cell sources, antibodies to FGIF can also be created. Antibodies may be polyclonal or monoclonal as desired. Monoclonal antibodies preferably target functionally active portions of the protein, such as the ankyrin site, and can be used in vitro or in vivo as agents that alter FGIF activity. Methods for the generation of both polyclonal and monoclonal antibodies from protein samples are well know to those of ordinary skill in the art (e.g. *Current Protocols in Immunology*, J. E. Coligan et al. (eds.), John Wiley & Sons, New York).

Another embodiment of the invention is directed to nucleic acid sequences that encode FGIF proteins, peptides and fragments, and functionally or structurally equivalent portions thereof. As before, methods for assessing functional and structural equivalency are well known and routine within the art. Functionally equivalent nucleic acid sequences include, for example, sequences that encode different, but equivalent FGIF polypeptides whose differences can be attributed to degeneracy of the genetic code. However, these FGIF polypeptides would also exhibit similar functional activity. In such cases, the respective nucleic acids encode functionally equivalent gene products.

In addition, functional fragments of FGIF encoding nucleic acids such as oligonucleotides, polyoligonucleotides, primers and the like are also within the definition of the term FGIF. Functional equivalency is also present with FGIF nucleic acids that do not encode gene products but, for example, are functional elements in and of themselves. Specific examples of such functional nucleic acids include promoters, enhancers and other gene expression regulatory elements.

Sequences encoding FGIF proteins, peptides and fragments may comprise DNA, RNA or PNA sequences which may be double-stranded or single-stranded. These sequences may comprise the nucleotides characteristic of DNA (e.g. A, G, C, T), RNA (e.g. A, G, C, U) or PNA (e.g nucleotide bases covalently connected to a polyamide backbone), or, alternatively, may contain one or more modified nucleotide bases. Modified bases include, for example, acetylcytidine, dihydrouridine, inosine, methylated bases, methoxyuridine and many others, all of which are well known to those of ordinary skill in the art.

FGIF sequences may also be inserted in prokaryotic or eukaryotic cells to form recombinant cells that express or are capable of expressing FGIF. For example, prokaryotic cells such as *E. coli* can be transformed with FGIF nucleic acid sequences. Eukaryotic cells can be transfected with FGIF nucleic acids or FGIF-containing nucleic acid vectors using procedures that are well-known in the art (e.g *Current Protocols in Molecular Biology*, F. M. Ausubel et al. (eds.), John Wiley & Sons, New York). Transfected sequences may be maintained as episomal or integrated into the host cell genome. FGIF protein can be continuously or, upon induction, selectively expressed from these cells as desired by incorporating transcriptional or translational control sequences such as promoters, enhancers, operators, termination sites, etc., all of which are well known to those of ordinary skill in the art. Recombinant cells containing FGIF sequences can be maintained, expanded to produce large quantities of nucleic acids, or induced to express large quantities of FGIF.

Another embodiment of the invention is directed to methods for the treatment of globin disorders by regulation of FGIF activity or expression. FGIF and agents that regulate FGIF expression can mediate the severity of globin disorders such as sickle cell anemia and thalassemia, and associated disorders by increasing or decreasing globin gene expression. For example, many globin disorders can be mediated by increased fetal globin gene expression. FGIF protein and peptides, and functional fragments thereof, or agents that alter FGIF activity can be used to activate fetal globin expression. Increased amounts of fetal globin have been shown to alleviate or cure globin disorders including the sickle cell syndromes and the β thalassemia syndromes. FGIF amino acid sequences can also be used to maintain expression of therapeutic quantities of fetal globin for the treatment of various hemoglobinopathies. FGIF protein can also be administered to patients to reduce globin expression. In many patients, complications arise due to the accumulation of excess alpha chains. Administering agents that decrease FGIF activity and thereby decrease alpha chain expression may alleviate such disorders or at least ameliorate symptoms associated with such disorders.

Expression of therapeutically effective quantities of FGIF can be achieved, for example, in hematopoietic cells by in vivo or ex vivo modes to augment expression of the endogenous globin genes. FGIF can be administered by delivering therapeutically effective quantities of protein or agents that regulate FGIF expression or activity. A therapeutical effective quantity is that amount which has a beneficial effect to the patient by alleviating one or more symptoms of the disorder or simply reduce premature mortality. For example, a beneficial effect may be a decrease in pain, a decrease in duration, frequency or intensity of crises, an increased hematocrit, an improved erythropoiesis, a reduced or eliminated necessity for chelation therapy, an increased reticulocyte count, an increased peripheral blood flow, a decreased hemolysis, decreased fatigue or an increased strength. Preferably, a therapeutic amount is that amount of chemical compound or agent delivered to a patient that stimulates or enhances the expression of non-adult globin such as embryonic or fetal globin, or the proliferation of embryonic, fetal or adult globin expressing cells.

The patient may be a domesticated animal, but is preferably a human or another primate. Administration may be to an adult, an adolescent, a child, a toddler, a neonate or an infant, or administered in utero. Administration of compositions of the invention containing FGIF or agents that affect FGIF expression or activity may be short term, continuous or sporadic as necessary. Patients with a suspected or diagnosed with a blood disorder may only require composition treatment for short periods of time or until symptoms have abated or have been effectively eliminated. Compositions provided to the patient may include any combination of the proteins or agents of the invention in combination with other substances such as chemical compounds known to those of ordinary skill in the art as useful for the treatment of globin disorders.

Compositions of the invention can be directly or indirectly administered to the patient. Indirect administration is performed, for example, by administering the composition to cells ex vivo and subsequently introducing the treated cells to the patient. The cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized.

Direct administration of a composition may be by oral, parenteral, sublingual, rectal such as suppository or enteral administration, or by pulmonary absorption or topical application. Parenteral administration may be by intravenous injection, subcutaneous injection, intramuscular injection, intra-arterial injection, intrathecal injection, intra peritoneal injection or direct injection or other administration to one or more specific sites. Injectable forms of administration are sometimes preferred for maximal effect in, for example, bone marrow. When long term administration by injection is necessary, venous access devices such as medi-ports, in-dwelling catheters, or automatic pumping mechanisms are also preferred wherein direct and immediate access is provided to the arteries in and around the heart and other major organs and organ systems.

Another effective method of administering the composition is by direct contact with, for example, bone marrow through an incision or some other artificial opening into the body. Compositions may also be administered to the nasal passages as a spray. Arteries of the nasal area provide a rapid and efficient access to the bloodstream and immediate access to the pulmonary system. Access to the gastrointestinal tract, which can also rapidly introduce substances to the blood stream, can be gained using oral, enema, suppository, or injectable forms of administration. Compositions may be administered as a bolus injection or spray as appropriate. Compositions may be given sequentially over time (episodically) such as every two, four, six or eight hours, every day (QD) or every other day (QOD), or over longer periods of time such as weeks to months. Compositions may also be administered in a timed-release fashion such as by using slow-release resins and other timed or delayed release materials and devices. Orally active compositions are more preferred as oral administration is usually the safest, most convenient and economical mode of drug delivery. However, direct injection may be preferred when immediate access to the blood system is desired.

Treatments to the patient may be therapeutic or prophylactic. Therapeutic treatment involves administration of one or more compositions of the invention to a patient suffering from one or more symptoms of the disorder. Symptoms typically associated with globin disorders include, for example, anemia, tissue hypoxia, organ dysfunction, abnormal hematocrit values, ineffective erythropoiesis, abnormal reticulocyte count, abnormal iron load, splenomegaly, hepatomegaly, impaired peripheral blood flow, dyspnea, increased hemolysis, jaundice, anemic crises and pain such as angina pectoris. Relief and even partial relief from one or more of these symptoms corresponds to an increased life span or simply an increased quality of life. Further, treatments that alleviate a pathological symptom can allow for other treatments to be administered.

Prophylactic treatments involve pulsed administration of a composition to a patient having a confirmed or suspected blood disorder without having any overt symptoms. For example, otherwise healthy patients who have been genetically screened and determined to be at high risk for the future development of a blood disorder may be administered compositions of the invention prophylactically. Administration can begin at birth and continue, if necessary, for life. Both prophylactic and therapeutic uses are readily acceptable because these compounds are generally safe and non-toxic.

Another embodiment of the invention is directed to a method for regulating the expression of a globin gene in a mammalian cell comprising exposing the cell to an effective amount of a composition of the invention. Upon exposure, a poorly expressed or quiescent globin gene of the cell is stimulated to increase the expression of its protein product. An effective amount of the composition is that amount which increases the extent or magnitude of hematopoiesis, increases the proliferation of hemoglobin expressing cells, increases, decreases or balances expression from one or more globin genes, or increases or stimulates the specific expression of one or more globin genes such as an alpha (α) globin gene, a zeta (ζ) globin gene, an epsilon (ε) globin gene, a beta (β) globin gene, a delta (δ) globin gene, a gamma (G-γ or A-γ) globin gene, or an, at least, partly functional pseudo-globin gene. Cells can be treated in culture or in vivo. Cultures of treated cells will produce increased amounts of hemoglobin and preferably embryonic or fetal globin. This hemoglobin can be harvested for introduction to a patient or the stimulated cells themselves can be administered to the patient. Alternatively, recombinant cells containing a globin gene which can be stimulated by compositions of the invention can be utilized. These recombinant cells may be heterologous or homologous natural cells, or synthetically created cells such as a lipid vesicles.

Alternatively administration may comprise the administration of quantities of nucleic acids that encode FGIF. Such nucleic acids can be administered in vivo in vector systems capable of expressing FGIF. Many such systems are well known to those of ordinary skill in the art and include, for example, adenovirus and adeno-associated virus vectors, retroviral vectors, liposomes and direct injection of expressible nucleic acids into cells. Such methods and vectors are described in, for example, Wolff et al. (Science 247:1465–1468, 1990; Ali et al., Gene Therapy, 1:367–384, 1994; Walsh et al., Proc. Natl. Acad. Sci. U.S.A., 91:7257–7261, 1994; Miller, Nature, 357:455–460, 1992; Michael and Curiel, Gene Therapy, 1:223–232, 1994; Budker et al., Gene Therapy, 3:593–598, 1996; Kay et al., Proc. Natl. Acad. Sci. U.S.A., 91:2353–2357, 1994; Hengge et al., Nat. Genet., 10: 161–166, 1995; Mann et al., Cell, 33:153–159, 1983; Nicolau et al., Proc. Natl. Acad. Sci. U.S.A., 80:1068–1072, 1983; and U.S. Pat. No. 5,399,346). These vector systems and many others also well known in the art can be used to express FGIF in hematopoietic target cells to augment fetal globin expression.

The expression of FGIF provides advantages for the treatment of globin disorders such as hemoglobinopathies over current therapies involving globin gene expression. For example, conventional vectors carrying either human fetal (γ) of human adult (β) globin genes for expression of therapeutic polypeptides. This approach requires a consistent production of high levels of globin mRNA in the target cell population which is difficult and often impractical to achieve with any degree of confidence. Expression of FGIF encoding nucleic acids overcomes these disadvantages as a relatively small numbers FGIF molecules transactivates expression of endogenous fetal globin genes.

Another embodiment of the invention is directed to methods of screening for agents that modulate FGIF function. Methods consist of contacting FGIF with a sample containing an agent to be tested and determining whether the agent enhances or inhibits the transactivation function of FGIF. Transactivation can be measured by determining the change in expression levels of fetal globin. Agents that enhance FGIF function can be used to treat hemoglobinopathies and β thalassemia syndromes.

Methods for screening can be performed using a variety of methods known in the art. Such assays include, for example, the use stable or transient expression or in vivo, expression assays. Other assays known in the art, including in vitro screening procedures are similarly applicable for identifying modulators of FGIF. Any or all of such assays can be automated or modified for high throughput procedures. Agents to be screened for presence of inducers of fetal globin gene expression include, for example, libraries of chemicals, pharmaceutical products or naturally existing substances.

Another embodiment of the invention is directed to agents identified by the above methods which induce globin gene expression and preferably fetal globin expression. Induction can be by either direct or indirect modes of action. Agents that directly induce fetal globin expression are agents that increase fetal globin transcription. Agents that indirectly induce expression are agents that regulate FGIF activity which thereby increases fetal hemoglobin expression. Agents that indirectly affect FGIF activity include butyric acid and butyric acid compounds.

The following examples illustrate embodiments of the invention, but should not be viewed as limiting the scope of the invention.

EXAMPLES

Hybrids formed by fusing human fetal erythroblasts (HFE) with mouse erythroleukemia (MEL) cells initially produce human γ-globin and subsequently switch to β-globin expression. Gamma (γ) gene expression in these hybrids can be explained by presence of fetal erythroid-origin trans acting factors that activate γ globin gene transcription. Factors present in fetal erythroid cells were cloned using differential mRNA display. With this method, mRNA species can be distinguished by the size of amplified cDNA fragments. By comparing cDNA species amplified from mRNA of γ-hybrids, β-hybrids, human fetal liver erythroblasts and adult erythroblasts, cDNAs present only in γ-hybrids and fetal liver erythroblasts and to functionally recognize those inducing γ gene transcription using transactivation assays were identified.

RNA was prepared from a single hybrid when it was at the stage of exclusive γ-globin expression or exclusively β-globin expression. mRNA was amplified using 5'-arbitrary primers and 3'-T12VN primers. Fifty pairs of cDNA fragments which were present both in human fetal liver erythroblasts and in the γ-hybrid, but absent in human adult erythroblasts and the β-hybrid, were cloned and sequenced. The sequences of 48 pairs differed between the fetal liver erythroblasts and the γ-hybrid, in spite of the identical sizes of amplified products. Two pairs had identical sequences in the fetal liver erythroblasts and the γ-hybrid. The mRNA of one of these pairs codes for human proteasome subunit X. The sequence of the second pair, designated as FL/H6, belongs to a previously unidentified human gene. Northern Blots using FL/H6 as a probe revealed two hybridization signals in human fetal liver cells, but only one in human adult bone marrow cells or MEL cells. A second hybridization signal with higher molecular weight was also found in a α-ABA-treated γ-hybrid, where the switching from human γ to β globin was strikingly delayed. Full-length cDNA (FGIF) of FL/H6 was cloned from a human fetal liver cDNA library as well as the α-ABA-treated γ-hybrids cDNA library.

The two cDNAs have over 80% homology at the nucleic acids level and over 85% homology in predicted open reading frame. In view of this data, FGIF sequences from other mammalian sources is expected to have corresponding degrees of homology. Protein translated from the cDNAs has three ankyrin motifs and limited homology with transcriptional factor Notch. The nucleotide sequences of FGIF is shown in FIGS. 1 and 2, and the amino acid sequence, in FIG. 3.

Transcriptional activation activity of FGIF was determined using a yeast transactivation assay. Briefly, yeast stably integrated with the LacZ reporter gene controlled by yeast Gal4 UAS and minimal promoter was transformed with either a control construct containing only the Gal4 DNA binding domain (pBD) or a construct containing a fusion of FGIF with a Gal4 DNA binding domain. Following transformation, and an initial expression period, transcriptional activation activity of FGIF was determined by measuring activation of the LacZ reporter gene. LacZ activities were determined in lysates of yeast colonies transformed with either pBD or pBD-FGIF. Relative luminescent units (RLU) were expressed per microgram of protein.

Figure 4:
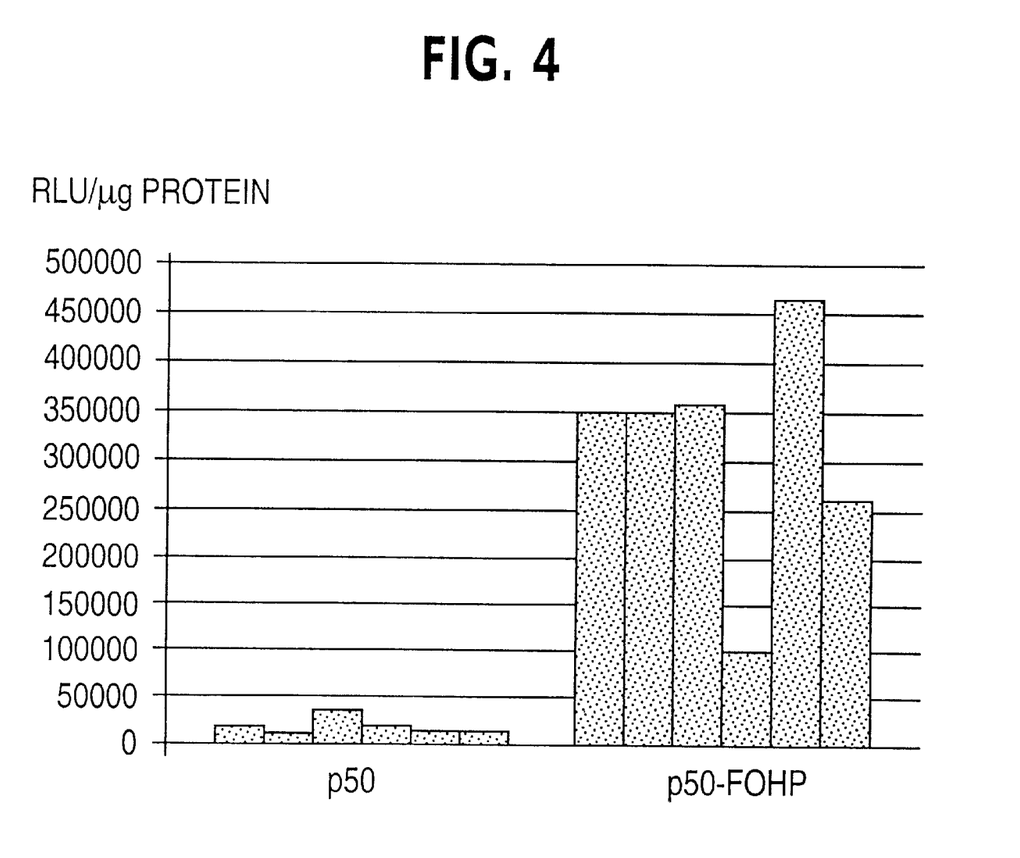
FIG. 4 FGIF function as a transcriptional activator.

A total of six pairs of control and pBD-FGIF transformed yeast colonies were examined. Relative luminescent units of these colonies is shown in FIG. 4. In all cases, significant transcription of between about 14–30 fold in the LacZ reporter gene was observed in the pBD-FGIF expressing colonies compared to controls. These results indicate that FGIF is a transcriptional transactivator.

Additional functional studies were performed to assess the induction of human γ globin gene expression by FGIF. Briefly, somatic cell hybrids which contained human chromosome 11 (the chromosome on which the human β globin locus resides) and which displayed low level of human fetal globin gene expression (about 5% of total human globin were γ), were stably transfected with an FGIF expression construct. Hybrids comprised human fetal erythroid×MEL cell hybrids. The FGIF construct, termed μLCR-β-FGIF-pA-SV40p-Neo-pA, was comprised of: μLCR which corresponds to a 2.5 kb cassette of the β globin locus control region; β which corresponds to the β globin gene promoter; pA which corresponds to a polyadenylation site, and Neo which corresponds to a neomycin resistance gene that confers resistance to the mammalian selectable agent G418. The μLCR-β promoter was used to allow erythroid lineage specific expression of FGIF.

Figure 5:
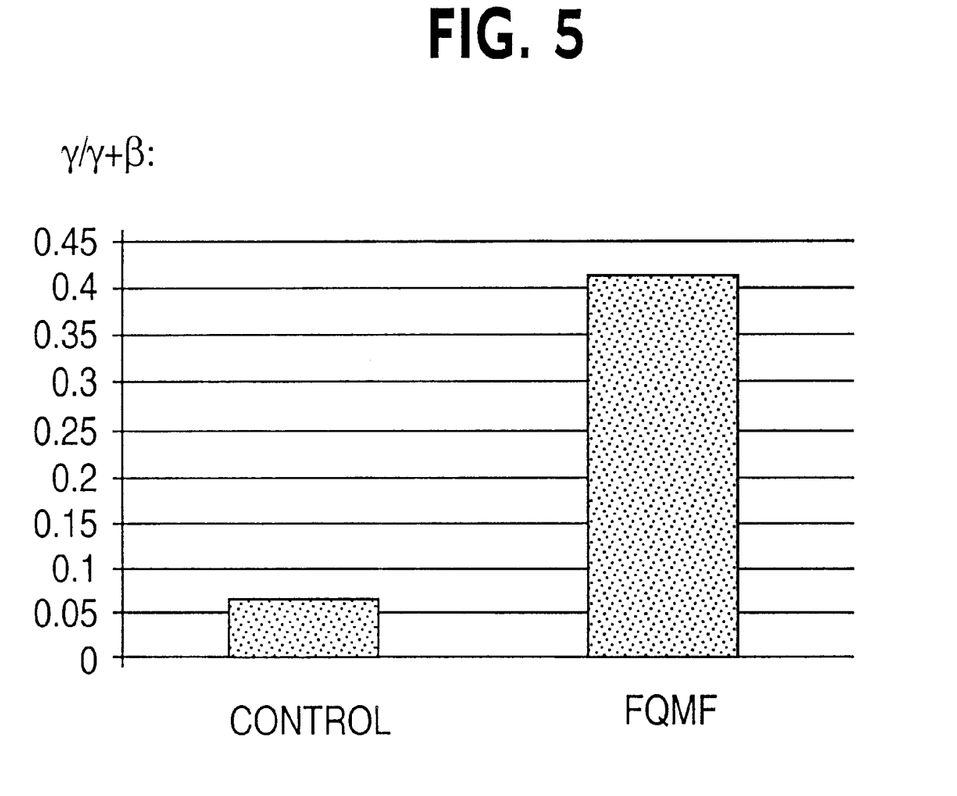
FIG. 5 Induction of human fetal globin by FGIF.

Stably transfected hybrids were selected with G418 and induced with hemin and HMBA. FGIF dependent expression of fetal globin was determined by RNASE protection assay. The results of these studies are shown in FIG. 5 and are expressed as the ratio of γ globin to γ+β globin expression. Hybrids expressing induced FGIF resulted in an about 8-fold higher γ/γ+β ratio than untransfected hybrids. Studies using anti-γ globin chain antibodies showed similar increase in γ globin positive cells indicating that the γ globin was also increased. These results indicate that FGIF functions in vivo as an inducer of Y globin. Untransfected hybrids were used as the control.

Other embodiments and uses of the invention will be apparent to those skilled in the art from consideration of the specification and practice of the invention disclosed herein. All U.S. patents and patent applications, including provisional application Ser. No. 60/033,247, entitled Fetal Globin Inducing Factor filed Dec. 5, 1996, and all other documents referenced herein, for whatever reason, are specifically incorporated by reference. It is intended that the specification and examples be considered exemplary only, with the true scope and spirit of the invention indicated by the following claims.

What is claimed is:

1. An isolated amino acid sequence or an active fragment of said sequence that functions to regulate expression of a globin gene wherein said sequence comprises SEQ ID NO:3 or SEQ ID NO:3 with one or more conservative amino acid substitutions.

2. The amino acid sequence of claim 1 which is a human sequence.

3. A composition comprising the amino acid sequence of claim 1 and a carrier.

4. The composition of claim 3 wherein the carrier is selected from the group consisting of water, oils, alcohols, salts, fatty acids, saccharides, polysaccharides and combinations thereof.

* * * * *

UNITED STATES PATENT AND TRADEMARK OFFICE
CERTIFICATE OF CORRECTION

PATENT NO.     : 6,184,343 B1
DATED          : February 6, 2001
INVENTOR(S)    : Stamatoyannopoulos et al.

It is certified that error appears in the above-identified patent and that said Letters Patent is hereby corrected as shown below:

<u>Title page,</u>
Item [76] Inventors: after the two inventors, please insert the third named inventor --
Yi Yang, 1038 NE 125th Street, Apt. 6, Seattle, Washington 98125 --.

<u>Column 12,</u>
Line 30, delete "Y" and insert -- $\gamma$ --.

Signed and Sealed this

Thirteenth Day of November, 2001

Attest:

NICHOLAS P. GODICI
Attesting Officer        Acting Director of the United States Patent and Trademark Office

SEQUENCE LISTING

<160> NUMBER OF SEQ ID NOS: 3

<210> SEQ ID NO 1
<211> LENGTH: 1318
<212> TYPE: DNA
<213> ORGANISM: Homo sapiens

<400> SEQUENCE: 1

```
gaacccggaa gtgagatgca aggcggcgat tttcccttct gtcagatctt gatgaacaaa      60
gcagtcataa ttcatctcta gaaagattta tatcctggca tttgaaatgc ttttattta     120 gaatagtagt aaaaaatgga aaaagaaaaa ggaaatgatg atggaatacc agaccaagag     180
aattccttgg atttttctga acactttagc caacttgaat tgttggaaac acatggacac     240
cttattccta ctggtactca aagtctttgg gtaggcaatt ctgatgaaga tgaggagcaa     300
gatgacaaaa atgaagagtg gtatcgattg caagaaaaaa aaatggaaaa agacccaagc     360
agattgcttc tttgggctgc tgaaaaaaat cggcttacca cagtgcggag actcctttct     420
```

```
gaaaaggcca ctcacgtgaa cactagggat gaagatgagt ataccctct tcatcgagca      480 gcctacagtg gacacttaga tattgttcag gagctcattg cacaggggc cgatgttcat      540 gcagtgactg tggatggctg gacgccctg cacagtgctt gtaagtggaa taataccaga      600
gtggcttctt tcttactgca gcatgatgca gatatcaatg cccaaacaaa aggcctcttg      660 accccttgc atcttgctgc tgggaacaga gacagcaagg ataccctaga actcctcctg      720
atgaaccgtt acgtcaaacc agggctgaaa acaacttgg aagaaactgc atttgatatt      780
gccaggagga caagtatcta tcactacctc ttttgaaattg tggaaggctg tacaaattct      840
tcacctcagt cttaacaatt ctagtaattt tcctaagttt ctaaatacca gtgcctcctg      900
tgtgtgagat gtattcccat aatcaaagtt gacgtcaaac atcttactac aaaaattcag      960
tgacattcat tataacattc ttccaagtga attgcctgac tttgatgtca atgtatttg       1020 aaagtaattt gcatatatct ttaattattt ctgtggagtt tgtgattttt ttatcagaaa      1080
taattttaat gtgtgtatac ttaaaaactt gacacgggtt gtacagaaac tggtattttt      1140
ggtgctgata caagagaaat gtattttaa atatcccaca tcctggatct ttgttgggta      1200
tttagtatat tgacatatat ttttataagg tgaggtaact cagaacttaa tttaaaagtc      1260
ttaaatattc tgatacaatt cagctgtctt ctctaccta ccatagccat gtctctgc         1318

<210> SEQ ID NO 2
<211> LENGTH: 1120
<212> TYPE: DNA
<213> ORGANISM: Murinae gen. sp.
<220> FEATURE:
<221> NAME/KEY: unsure
<222> LOCATION: (21)
<223> OTHER INFORMATION: Can be a or g or c or t/u
<220> FEATURE:
<221> NAME/KEY: unsure
<222> LOCATION: (27)
<223> OTHER INFORMATION: can be a or g or c or t/u
<220> FEATURE:
<221> NAME/KEY: unsure
<222> LOCATION: (63)
<223> OTHER INFORMATION: can be a or g or c or t/u
<220> FEATURE:
<221> NAME/KEY: unsure
<222> LOCATION: (179)
<223> OTHER INFORMATION: can be a or g or c or t/u
<220> FEATURE:
<221> NAME/KEY: unsure
<222> LOCATION: (295)
<223> OTHER INFORMATION: can be a or g or c or t/u
<220> FEATURE:
<221> NAME/KEY: unsure
<222> LOCATION: (960)
<223> OTHER INFORMATION: can be a or g or c or t/u
<220> FEATURE:
<221> NAME/KEY: unsure
<222> LOCATION: (962)
<223> OTHER INFORMATION: can be a or g or c or t/u

<400> SEQUENCE: 2
aacccggaaa ggaagttctc ngtgagnttc tctctgtgaa aggttagaaa gaatcaaaca      60
atncagacat aattcatctc cttaaagatt gcgccctagt acttgaaatg cttttttattt     120 aaagagtag taaaaatgga aaaagaaaaa aaggatgatg aaaaaccaga ccaggaaanc      180
tctgtggact tttctgaaca gtttaaccag cttgaattgt tgaaaactca tggacacctg      240
attcccactg gtactcagag tctctgggta ggcaattctg atgaagatga agagnaagag      300
gaaaaaaacg aagagtggta ccaattgcaa gaaaaaaaga tggaaaaaga tccaagcaaa      360
```

-continued

```
ttgcttcttt gggctgctga aaaaaatcgg cttgctacag tgcagagact actctctgag    420
aaggccgctg aagtgaacac tagggatgaa gatgagtata cccctcttca ccgagcagcc    480
tacagtgggc atatagatgt tgttcgtgag ctggtggcta aggggcaga tgttcatgca     540 gtgactgtgg atggctggac accactgcat agtgcttgta agtggaataa taccaaggtg    600
gcctctttct tacttcagca tgatgcagac atcaacgccc aaacgaaagg ccttttgacc    660
cctttgcacc ttgctgctgg gaacagagac agcagagaca ctctggaact cctcctgatg    720
aatcgttaca tcaaaccaga gctgaagaac aactcacaag aaactgcttc tgatatcgcc    780
aggaggacaa gcatctatca ctacctcttt gaaattgcgg aaggctgtac aaactcttca    840
cctccgtctt aatgactcta gtaatttaaa gtttcaaagt accagtgcct cccatgtgtg    900
agatgtaaaa tattcccatg tacagagaaa agatgtctca ctacagaagt tctgttgtgn    960
gnatcacagc tttcttccaa gtaagctgcc cgaccttgat gtcacatgta tttgagaggt    1020
atttgggtac atctgtggag atttctgcag tgtgtggttt ttatcagaaa taattttgca    1080
ggacacaggt aatacagaaa ctaaggatat tttttggtgc                         1120
```

<210> SEQ ID NO 3
<211> LENGTH: 239
<212> TYPE: PRT
<213> ORGANISM: Homo sapiens

<400> SEQUENCE: 3

```
Met Glu Lys Glu Lys Gly Asn Asp Asp Gly Ile Pro Asp Gln Glu Asn
 1               5                  10                  15

Ser Leu Asp Phe Ser Glu His Phe Ser Gln Leu Glu Leu Leu Glu Thr
                20                  25                  30

His Gly His Leu Ile Pro Thr Gly Thr Gln Ser Leu Trp Val Gly Asn
            35                  40                  45

Ser Asp Glu Asp Glu Gln Asp Asp Lys Asn Glu Trp Tyr Arg
        50                  55                  60

Leu Gln Glu Lys Lys Met Glu Lys Asp Pro Ser Arg Leu Leu Leu Trp
65                  70                  75                  80

Ala Ala Glu Lys Asn Arg Leu Thr Thr Val Arg Arg Leu Leu Ser Glu
                85                  90                  95

Lys Ala Thr His Val Asn Thr Arg Asp Glu Asp Glu Tyr Thr Pro Leu
            100                 105                 110

His Arg Ala Ala Tyr Ser Gly His Leu Asp Ile Val Gln Glu Leu Ile
        115                 120                 125

Ala Gln Gly Ala Asp Val His Ala Val Thr Val Asp Gly Trp Thr Pro
    130                 135                 140

Leu His Ser Ala Cys Lys Trp Asn Asn Thr Arg Val Ala Ser Phe Leu
145                 150                 155                 160

Leu Gln His Asp Ala Asp Ile Asn Ala Gln Thr Lys Gly Leu Leu Thr
                165                 170                 175

Pro Leu His Leu Ala Ala Gly Asn Arg Asp Ser Lys Asp Thr Leu Glu
            180                 185                 190

Leu Leu Leu Met Asn Arg Tyr Val Lys Pro Gly Leu Lys Asn Asn Leu
        195                 200                 205

Glu Glu Thr Ala Phe Asp Ile Ala Arg Arg Thr Ser Ile Tyr His Tyr
    210                 215                 220

Leu Phe Glu Ile Val Glu Gly Cys Thr Asn Ser Ser Pro Gln Ser
225                 230                 235
```